US005821398A

United States Patent [19]
Speirs et al.

[11] Patent Number: 5,821,398
[45] Date of Patent: Oct. 13, 1998

[54] DNA MOLECULES ENCODING INDUCIBLE PLANT PROMOTERS AND TOMATO ADH2 ENZYME

[75] Inventors: James Speirs, Adelaide; Colin John Brady, Sheal Bay; Elizabeth Lee, Marsfield; Richard Hinde, Thornleigh; Terrence James Longhurst, Mt. Colah, all of Australia

[73] Assignee: Commonwealth Scientific & Industrial Research Org., Campbell Act, Australia

[21] Appl. No.: 448,600

[22] PCT Filed: Dec. 15, 1993

[86] PCT No.: PCT/AU93/00654

§ 371 Date: Jul. 26, 1995

§ 102(e) Date: Jul. 26, 1995

[87] PCT Pub. No.: WO94/13797

PCT Pub. Date: Jun. 23, 1994

[30] Foreign Application Priority Data

| Dec. 15, 1992 | [AU] | Australia | PL 6349 |
| May 26, 1993 | [AU] | Australia | PL 9059 |
| Aug. 19, 1993 | [AU] | Australia | PM 0712 |
| Aug. 19, 1993 | [AU] | Australia | PM 0713 |

[51] Int. Cl.[6] .......................... C12N 15/00; C07H 21/04; C12P 19/34
[52] U.S. Cl. ................... 800/205; 435/91.31; 435/172.1; 435/172.3; 536/23.1; 536/23.2; 536/24.1; 536/124.5
[58] Field of Search .............................. 435/91.31, 172.1, 435/172.3; 536/23.1, 23.2, 24.1, 24.5; 800/205

[56] References Cited

U.S. PATENT DOCUMENTS

| 4,987,071 | 1/1991 | Cech et al. | 435/91.31 |
| 5,254,678 | 10/1993 | Haseloff et al. | 536/23.2 |

FOREIGN PATENT DOCUMENTS

| 60423/90 | 2/1991 | Australia . |
| 65338/90 | 5/1991 | Australia . |
| 74350/91 | 7/1991 | Australia . |
| A74350/91 | 7/1991 | Australia . |
| 13690/92 | 10/1992 | Australia . |
| 32622/93 | 7/1993 | Australia . |
| 0 409 625A1 | 1/1991 | European Pat. Off. . |
| 409625 | 1/1991 | European Pat. Off. . |
| WO91/01375 | 2/1991 | WIPO . |
| WO91/05865 | 5/1991 | WIPO . |
| WO 91/16426 | 10/1991 | WIPO . |
| WO92/16635 | 10/1992 | WIPO . |
| WO93/14212 | 7/1993 | WIPO . |

OTHER PUBLICATIONS

Reeck et al. "Homology" in proteins and nucleic acids: a terminology muddle and a way out of it. Cell. 50:667, 1987.
Lewin, R. When does homology mean something else? Science. 237:1570, 1987.
Cuozzo et al. Viral protection in transgenic tobacco plants expressing the cucumber mosaic virus cost protein or its antisense RNA. Bio/Technology. 6(5):549–557, 1988.
Mazzolini et al. Assaying synthetic ribozymes in plants: high–level expression of a functional hammerhead structure fails to inhibit target gene activity in transiently transformed protoplasts. Plant Molecular Biology. 20:715–731, 1992.
Kiim et al. A 20 nucleotide upstream element is essential for the nopaline synthase (nos) promoter activity. Plant Molecular Biology. 24:105–117, 1994.
Bird et al. The tomato polygalacturonase gene and ripening–specific expression in transgenic plants. 11:651–662, 1988.
"Organization of Ripening and Ethylene Regulatory Regions in a Fruit–Specific Promoter from Tomato," Jill Deikman et al., *Plant Physiology*, vol. 100, Dec. 1992, pp. 2013–2017.
"Interaction of a DNA binding factor with the 5'–flanking region of an ethylene–responsive fruit ripening gene from tomato," Jill Deikman and Robert L. Fischer, *The EMBO Journal*, vol. 7, No. 11, 1988, pp. 3315–3320.
"Expression of a Chimeric Polygalacturonase Gene in Transgenic rin (Ripening Inhibitor) Tomato Fruit Results in Polyuronide Degradation but not Fruit Softening," James J. Giovannoni et al., *The Plant Cell*, vol. 1, Jan. 1989, pp. 53–63.
"Nucleotide sequence of alcohol dehydrogenase gene in octoploid strawberry (Frageria×Ananassa Duch.)," D.J. Wolyn et al., *Plant Molecular Biology*, vol. 14, 1990, pp. 855–857.
"Tomato alcohol dehydrogenase Expression during fruit ripening and under hypoxic conditions," D. Van Der Straeten et al., *FEBS Letters*, vol. 295, Dec. 1991, pp. 39–42.
"Lycopersicon esculentum alcohol dehydrogenase–2 (adh2) mRNA, complete cds," A.L. Genez et al., *EMBL Sequence Database*, Jul. 1992.
"Tomato Alcohol Dehydrogenase: Purification and Substrate Specificity," Thomas A. Bicsak et al., *Archives of Biochemistry and Biophysics*, vol. 216, No. 2, Jul. 1982, pp. 605–615.
"Developmental Research of the Expression of Alcohol Dehydrogenase in Ripening Tomato Fruits," T.J. Longhurst et al., *Journal of Food Biochemistry*, 14 (1990) pp. 421–433.
"Suppression of Cellulase and Polygalacturonase and Induction of Alcohol Dehydrogenase Isoenzymes in Avocado Fruit Mesocarp Subjected to Low Oxygen Stress," *Plant Physiol*, 96 (1991), pp. 269–274.

(List continued on next page.)

*Primary Examiner*—Douglas W. Robinson
*Assistant Examiner*—Thanda Wai
*Attorney, Agent, or Firm*—Lowe, Price, LeBlanc & Becker

[57] ABSTRACT

An isolated DNA molecule comprising a nucleotide sequence encoding an inducible soft fruit promoter, particularly the alcohol dehydrogenase 2 promoter from tomato, is described. Isolated DNA molecules encoding the alcohol dehydrogenase 2 enzyme are also disclosed.

23 Claims, 1 Drawing Sheet

OTHER PUBLICATIONS

Van der Straeton et al., "Cloning and sequence of two different cDNAs encoding 1–aminocyclopropane–1– carboxylate synthase in tomato", Proc. Natl. Acad. Sci. U.S.A., vol. 87, pp. 4859–4863, Jun. 1990.

Speirs et al., University of California conference abstract, "Induction of Tomato ADH 2 Gene in Normally Ripening Fruit and in Fruit Exposed to Hypoxia", 17–19 Aug. 1992.

Genez et al., Genebank "New Release" publication of an ADH2 cDNA sequence, Isolation of a tomato alcohol dehydrogenase 2 by phage promoted antibody screening of a plasmid cDNA library, approx. 15 May 1993.

Van der Straeton et al., "Tomato alcohol dehydrogenase Expression suring fruit ripening and under hypoxic conditions", FEBS Letters, 295, #1,2,3, pp. 39–42, Dec. 1991.

Tanksley et al. "Effects of $O_2$ Stress on Tomato Alcohol Dehydrogenase Activity: Descrip. of a Second ADH Coding Gene", Biochemical Genetics, 19, Nos. 3/4, 1981, pp. 397–409.

Kruger, K. et al., "Self–Splicing RNA: Autoexcision and Autocyclization of the Ribosomal RNA Intervening Sequence of Tetrahymena", Cell, vol. 31, pp. 147–157, Nov. 1982.

Ellis, J.G. et al., "Expression of a maize promoter in transgenic tobacco", EMBO Journal, vol. 6, pp. 11–16, 1987.

Olive, M.R. et al., "Functional properties of the anaerobic responsive element of the maize Adh1 gene", Plant Molecular Biology, vol. 15, pp. 593–604, 1990.

Haseloff, J. et al., "Simple RNA enzymes with new and highly specific endoribonuclease activities", Culture, vol. 334, 18, Aug. 1988, pp. 585–591.

Grierson et al. "The appearance of polygalacturonase mRNA in tomatoes: one of a series of changes in gene expr. during development and ripening", Planta, 163, 1983, pp. 263–271.

Sato, T. et al., "Polygalacturonase mRNA of Tomato: Size and Content in Ripe Fruits", Plant Cell. Physiol. vol. 26, No. 1, pp. 211–214, 1985.

DellaPena, D. et al., "In Vitro Synthesis and Processing of Tomato Fruit Polygalacturonase", Plant Physiol., vol. 86, pp. 1057–1063, 1988.

Speirs, J. et al., "Endopolygalacturonase: Messenger RNA, Enzyme and Softening in the Ripening Fruit of a Range of Tomato Genotypes", J. Plant Physiol., 135, 576–582, 1989.

Matton, Daniel P. et al., "Alcohol dehydrogenase gene expression in potato following elicitor and stress treatment", Plant Molecular Biology, vol. 14, pp. 775–783, 1990.

Lincoln, J.E. et al., "Diverse mechanisms for the regulation of ethylene–inducible gene expression", Mol. Gen. Genet., vol. 212, pp. 71–75, 1988.

Genez, A.L. et al., "Isolation of a tomato alcohol dehydrogenase 2–encoding cDNA using phage–promoted antibody screening of a plasmid cDNA library", Gene, 123, 157–64, 1993.

"Isolation of a Tomato Alcohol Dehydrogenase 2–Encoding CDNA Using Phage–Promoted Antibody Screening of a Plasmid cDNA Library", by Genez et al, Gene, vol. 123 (No. 2), issued 1993, pp. 157–164.

"Effects of $O_2$ Stress on Tomato Alcohol Dehydrogenase Activity: Description of a Second ADH Coding Gene", by Tanksley et al, Biochemical Genetics, vol. 19 (Nos. 3/4), issued 1981, pp. 397–409.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 2147 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
ATGTCGACTA  CTGTAGGCCA  AGTCATTCGT  TGCAAAGGTA  TAATAATTCC  ATGATTCTGT      60
AATTTCCTCG  TTTTTTTTTT  TAAGTTTGAT  AATTTTTGTG  GTAATTATAT  ATTATTTATA     120
GCTGCTGTGG  CATGGGAAGC  TGGTAAGCCA  TTAGTGATGG  AGGAAGTAGA  TGTTGCTCCT     180
CCACAGAAAA  TGGAAGTTCG  TCTTAAGATC  CTCTATACTT  CACTCTGTCA  TACTGATGTA     240
TACTTCTGGG  AAGCTAAGGT  AAACAAAACT  AAATTACGGG  ACTACGTTGA  GTATGTTAGT     300
GTTGTCAGCA  AATTTTATAA  GGGGATTATT  TCCTTTGAAC  TGATTTCAGG  GTCAAAATCC     360
AGTCTTTCCT  CGAATTCTTG  GACATGAAGC  AGCAGGGTAT  GTGTTATCTT  GTTTCAATTG     420
ATTGATTTGA  ATTCATCATT  TACTGTTTCT  AAAGCTAAAA  GGGTACTGAA  TTTTGTTGTC     480
TTCTTGATAT  TTAGGATTGT  GGAGAGTGTT  GGAGAGGGAG  TAACAGACCT  TGCACCAGGA     540
GACCATGTTC  TTCCTGTCTT  TACAGGGGAA  TGTAAAGATT  GTGCTCACTG  TAAATCTGAA     600
GAAAGCAATA  TGTGTAGCCT  CTTAAGGATT  AACACTGACA  GGGGAGTGAT  GCTTAATGAT     660
GGAAAATCAA  GATTTTCCAT  CAATGGAAAC  CCCATTTACC  ATTTGTTGG   GACCTCTACT     720
TTTAGTGAGT  ACACCGTGGT  TCATGTTGGA  TGTGTTGCAA  AAATTAACCC  TCTTGCTCCT     780
CTTGACAAAG  TATGTGTCCT  TAGTTGTGGA  ATTTCGACAG  GTATAGACGA  AGACAACGAT     840
AGATTATGTT  ACTAGTTTCT  TTTTAAGGAG  CTGCTCAATT  GTTGATTGAT  ATGAATACTT     900
TTCCAGGCCT  TGGAGCAAGT  TTGAATGTTG  CTAAACCAAC  AAAAGGCTCA  AGTGTGGCTA     960
TATTTGGACT  AGGAGCTGTA  GGCCTCGCGG  TGAGTATGCT  CCGTTGTGTT  GTTTATTGT    1020
TTCCCGTATA  TGTGTTAGTC  TTACAGATGA  CTGACTCATT  TGGTCAGGCT  GCAGAAGGAG    1080
CCAGAATTGC  TGGTGCCTCG  AGGATAATTG  GTGTTGATTT  AAATGCTAGT  AGATTTGAGC    1140
AAGGTAATAT  AAATTTTTCC  TTATACATTA  TCTTAAAATT  CCTTAGTAAA  ACAACTAATT    1200
CATCCATTTT  ACTTGTATTC  TACAGCTAAG  AAATTTGGTG  TGACAGAGTT  TGTGAACCCA    1260
AAGGACTATA  GTAAACCAGT  TCAAGAGGTA  CTCAAATCAT  ATTTAATTTA  CTTTAATCGA    1320
AGAAGAAAAA  AGACAGGTCT  GAGTTAATAG  TTGATGTCTT  TTCTTGAATT  CTGATTATTT    1380
GATCAGGTAA  TTGCTGAGAT  GACTGATGGC  GGAGTCGATA  GGAGTGTGGA  ATGTACGGGT    1440
CACATTGATG  CTATGATTTC  AGCATTTGAA  TGTGTCCATG  ATGTATGTTT  TCTGTAATCA    1500
AATTAATTTC  CTTAGCTGTA  TGTTTGCGTT  CATCTTAACG  AACATTGTTG  TATTAACTTT    1560
AGGGCTGGGG  AGTCGCGGTT  CTTGTTGGTG  TACCCCATAA  AGAAGCTGTG  TTCAAGACAC    1620
ATCCTCTGAA  CTTTTTGAAT  GAACGGACTC  TCAAAGGAAC  CTTCTTTGGA  AACTACAAAC    1680
CTCGTTCGGA  TATTCCTTGT  GTTGTTGAGA  AATACATGAA  CAAAGAACTT  GAATTGGAGA    1740
AATTCATCAC  TCATACACTT  CCATTTGCTG  AAATCAATAA  GGCTTTCGAT  TTAATGCTGA    1800
AGGGAGAAGG  CCTTCGTTGC  ATCATCACCA  TGGCGGACTA  AACTTTCTGT  CCTAGAAAAG    1860
```

-continued

| | | | | | |
|---|---|---|---|---|---|
|GAGCTTCTAC|TGTTTGAGAA|AAAAGACCAA|TAAATTGTCA|CTGTCTTATT|TTCCCTTTCG|1920|
|TGTTTGGTTG|AGTTGTAACA|TTCCATCCAT|GTCTCTTCTT|TTGTCTTTTG|CTTAGATGTT|1980|
|GTGCTTTGCC|ATATCTCTTT|CGATTCTTGT|AAAAAATGCA|AATTCTCTCT|GTTTTATCTC|2040|
|AAGTATATTT|ACAGAATTTC|AGTGATTTGA|TAAATCTAAA|CTTTATCATA|ATATAATCCA|2100|
|AACAGAATTT|CAATTGAAAA|TGATGAAGCC|CTTACCGTCA|TTGTTCC| |2147|

( 2 ) INFORMATION FOR SEQ ID NO:2:

( i ) SEQUENCE CHARACTERISTICS:
        ( A ) LENGTH: 940 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | |
|---|---|---|---|---|---|
|GATCAAAAGA|TGAACTAAGG|ATAATATTTT|TGATATTTTA|CCTTTTTTTT|AATTATAACG|60|
|TTGTTAAGAT|ATCAAAGGAC|CAATTATAAG|AAAACCACCC|AAAGGTTTCA|TGTTTTGATT|120|
|GAAAAAACCA|TCAAACAACG|CAATACAACT|GCTCAACTAG|AATCAACATA|ACAAAAAAAT|180|
|ATACTTAATG|AGATCATTTA|TAACCTAAAT|TATAACCCCT|CCGTGCACTT|TCATTTATCA|240|
|TGTTATATTT|TACGCAAGTC|AATTTGATTC|ATTTTAAAAG|TTAAATGAGA|TTATATTAAT|300|
|TTAATATTTT|AAATAAAATT|TTCAGATATT|TAAAAATTAT|ATGAAAAGTA|TCATGAATTG|360|
|TAGTTTTTTT|TTGCATATAT|GAAAAAATAC|ATTATAAATA|TTAGTCAATT|TTTTTATAAT|420|
|TTGACTCTAA|ATATGAAAAA|AAATGACAAT|TAAAAATAGA|CGGAGGTTGT|AAATTAGCTT|480|
|ATTAATTATT|AATTTGATAA|ATATCATAAT|TAACTGATAA|TGACAATTAA|ATATTTAGAA|540|
|GACGATAATG|ACAGAAATCA|ACGTTATTTT|AGGTATAATT|TTTGTTGTAT|TTTTGAAAAA|600|
|AATAATCTTT|TTTCTGCAAC|TGGTTATATT|AAGTGAACAA|ACAAAAAACA|AGTAGTATAA|660|
|AAAAATTACA|AGTGGACATA|AAACAAAATG|AGATACAGTA|TTTGTGTTTC|CATTGGAATA|720|
|TTAGCTTGAC|AAAAACTCAA|ACGAGCAACA|CAAAACAAAC|AGCTAAAAAA|CCTGTTTTGA|780|
|AAAATCCAGT|GACCAAAACA|TGTAAATGGT|TTTACTGTGG|CCTATTGTTT|TTTCACCTTT|840|
|CCCAATTATA|AATATCCACT|GCCTCAACTG|AGTAAACAAC|CAAAATTTGT|GTTCTATAAA|900|
|AAGTTTTCAT|ATTTAGTGAT|CACTAAAAAA|AAATCAAGAA| | |940|

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

Met  Ser  Thr  Thr  Val  Gly  Gln  Val  Ile  Arg  Cys  Lys
    1                 5                         10

( 2 ) INFORMATION FOR SEQ ID NO:4:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

```
Ala  Ala  Val  Ala  Trp  Glu  Ala  Gly  Lys  Pro  Leu  Val  Met  Glu  Glu  Val
 1              5                        10                       15

Asp  Val  Ala  Pro  Pro  Gln  Lys  Met  Glu  Val  Arg  Leu  Lys  Ile  Leu  Tyr
              20                   25                       30

Thr  Ser  Leu  Cys  His  Thr  Asp  Val  Tyr  Phe  Trp  Glu  Ala  Lys
         35                   40                       45
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Gly  Gln  Asn  Pro  Val  Phe  Pro  Arg  Ile  Leu  Gly  His  Glu  Ala  Ala  Gly
 1              5                        10                       15
```

( 2 ) INFORMATION FOR SEQ ID NO:6:

( i ) SEQUENCE CHARACTERISTICS:
        ( A ) LENGTH: 109 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:6:

```
Ile  Val  Glu  Ser  Val  Gly  Glu  Gly  Val  Thr  Asp  Leu  Ala  Pro  Gly  Asp
 1              5                        10                       15

His  Val  Leu  Pro  Val  Phe  Thr  Gly  Glu  Cys  Lys  Asp  Cys  Ala  His  Cys
              20                   25                       30

Lys  Ser  Glu  Glu  Ser  Asn  Met  Cys  Ser  Leu  Leu  Arg  Ile  Asn  Thr  Asp
         35                   40                       45

Arg  Gly  Val  Met  Leu  Asn  Asp  Gly  Lys  Ser  Arg  Phe  Gly  Ile  Asn  Gly
    50                        55                   60

Asn  Pro  Ile  Tyr  His  Phe  Val  Gly  Thr  Ser  Thr  Phe  Ser  Glu  Tyr  Thr
65                       70                   75                       80

Val  Val  His  Val  Gly  Cys  Val  Ala  Lys  Ile  Asn  Pro  Leu  Ala  Pro  Leu
                   85                        90                       95
```

```
         Asp  Lys  Val  Cys  Val  Leu  Ser  Cys  Gly  Ile  Ser  Thr  Gly
                   100                      105
```

( 2 ) INFORMATION FOR SEQ ID NO:7:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

```
    Leu  Gly  Ala  Ser  Leu  Asn  Val  Ala  Lys  Pro  Thr  Lys  Gly  Ser  Ser  Val
    1                   5                        10                       15
    Ala  Ile  Phe  Gly  Leu  Gly  Ala  Val  Gly  Leu  Ala
                   20                      25
```

( 2 ) INFORMATION FOR SEQ ID NO:8:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
    Ala  Ala  Glu  Gly  Ala  Arg  Ile  Ala  Gly  Ala  Ser  Arg  Ile  Ile  Gly  Val
    1                   5                        10                       15
    Asp  Leu  Asn  Ala  Ser  Arg  Phe  Glu  Gln
                   20                      25
```

( 2 ) INFORMATION FOR SEQ ID NO:9:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

```
    Ala  Lys  Lys  Phe  Gly  Val  Thr  Glu  Phe  Val  Asn  Pro  Lys  Asp  Tyr  Ser
    1                   5                        10                       15
    Lys  Pro  Val  Gln  Glu
                   20
```

( 2 ) INFORMATION FOR SEQ ID NO:10:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:10:

```
Val  Ile  Ala  Glu  Met  Thr  Asp  Gly  Gly  Val  Asp  Arg  Ser  Val  Glu  Cys
1                   5                        10                       15
Thr  Gly  His  Ile  Asp  Ala  Met  Ile  Ser  Ala  Phe  Glu  Cys  Val  His  Asp
                    20                  25                       30
```

( 2 ) INFORMATION FOR SEQ ID NO:11:

( i ) SEQUENCE CHARACTERISTICS:
　　　　( A ) LENGTH: 92 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:11:

```
Gly  Trp  Gly  Val  Ala  Val  Leu  Val  Gly  Val  Pro  His  Lys  Glu  Ala  Val
1                   5                        10                       15
Phe  Lys  Thr  His  Pro  Leu  Asn  Phe  Leu  Asn  Glu  Arg  Thr  Leu  Lys  Gly
                    20                  25                       30
Thr  Phe  Phe  Gly  Asn  Tyr  Lys  Pro  Arg  Ser  Asp  Ile  Pro  Cys  Val  Val
               35                  40                  45
Glu  Lys  Tyr  Met  Asn  Lys  Glu  Leu  Glu  Leu  Glu  Lys  Phe  Ile  Thr  His
          50                   55                       60
Thr  Leu  Pro  Phe  Ala  Glu  Ile  Asn  Lys  Ala  Phe  Asp  Leu  Met  Leu  Lys
65                       70                       75                       80
Gly  Glu  Gly  Leu  Arg  Cys  Ile  Ile  Thr  Met  Ala  Asp
                    85                       90
```

( 2 ) INFORMATION FOR SEQ ID NO:12:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

CCACTGCCTC AACTGAG　　　　　　　　　　　　　　　　　　　　　　　　　　　　17

( 2 ) INFORMATION FOR SEQ ID NO:13:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

-continued (iii) HYPOTHETICAL: NO (iv) ANTI-SENSE: NO (xi) SEQUENCE DESCRIPTION: SEQ ID NO:13:

CGACCATTCG GTAATCA                                                                                       1 7

DNA MOLECULES ENCODING INDUCIBLE PLANT PROMOTERS AND TOMATO ADH2 ENZYME

This application is a 371 PCT/AU93/00654, filed on Dec. 15, 1993, published as WO94/13797 Jun. 23, 1994.

This invention relates to inducible plant promoter DNA sequences, DNA sequences encoding tomato alcohol dehydrogenase 2 (ADH2) enzyme, and hybrid DNA molecules incorporating such sequences. In a particular application of the invention, these hybrid DNA molecules are used to transform plants to enable the control of the condition and quality of fruit.

In the soft fruit industry (e.g. strawberries, peaches, plums and tomatoes), substantial losses are incurred during transport, storage and marketing because of the susceptibility of softer fruit to mechanical damage and invasion by microorganisms. To limit such losses, plant breeders have selected lines which are less soft, and for many fruits firm cultivars now dominate national and international trade. Unfortunately, while marketing losses may be lower when fruit is less soft, the firmer lines may have reduced market appeal and also tend to be deficient in flavour.

In some fruits, such as tomatoes, avocadoas and peaches, softening arises from the degradation of cell wall components by enzymes deposited in response to signals associated with ripening. Ripening signals typically include ethylene and the fruit response to ethylene and other signals can be strongly affected by temperature, and by oxygen and carbon dioxide concentrations. In firm fruit cultivars, the response to ripening signals has usually been damped so that less enzyme is produced; softening is correspondingly protracted and unless the signal response can be enhanced, by the time the fruits are acceptably soft the tissue is often senescent and lacking in flavour and aroma.

In higher organisms, structural genes, including those involved in softening and the development of flavour and aroma in fruit, are switched on by DNA sequences known as promoters, which recognise internal signals and "promote" transcription of the adjacent functional genes. Promoters which respond to oxygen stress or to heat shock have been characterised in plants, for example alcohol dehydrogenase (ADH) accumulates in plants after 5 to 10 hours of oxygen stress, and heat shock proteins can be detected after only brief periods of high temperature. In each case the new chemical entities are produced through the response of promoters to environmental signals. Thus, these kinds of inducible promoters permit the construction of hybrid DNA molecules in which a structural gene encoding, for example, a polypeptide involved in fruit softening, is brought under the control of an inducible promoter sequence, so that the structural gene is transcribed when the promoter is subjected to an activating signal.

Accordingly, in a first aspect the present invention provides an isolated DNA molecule comprising a nucleotide sequence encoding a soft fruit promoter or functional portion thereof, wherein said promoter or functional portion thereof is characterised in that it can be activated by environmental agents or conditions and/or is activated, or primarily activated, during a late stage of normal soft fruit ripening.

Preferably the soft fruit promoter or functional portion thereof is activated thermally, chemically or by light. In the case of chemical activation, preferred promoters and functional portions thereof will be responsive to particular levels of gases such as oxygen, carbon dioxide or carbon monoxide. Alternatively, chemical activation may be achieved through exposure to some organic acids.

The soft fruit promoter or functional portion thereof may be isolated from grapes, strawberries, peaches, plums or tomatoes. Preferably the soft fruit promoter or functional portion thereof is activated by environmental agents or conditions, and is further characterised by also being activated, or primarily activated, during a late stage of normal ripening. For example, for tomato, during the period of ripening following 5–6 days after ripening-onset. More preferably, the promoter or functional portion thereof is the tomato alcohol dehydrogenase 2 (ADH2) promoter.

Thus, in a second aspect the present invention provides an isolated DNA molecule comprising a nucleotide sequence encoding, or substantially homologous to, the tomato ADH2 promoter or a functional portion thereof.

The term "substantially homologous" as used herein in relation to the nucleotide sequence encoding the tomato ADH2 promoter or functional portion thereof, is intended to encompass nucleotide sequences with sufficient homology to hybridise to the nucleotide sequence encoding the tomato ADH2 promoter or functional portion thereof under medium to high stringency conditions (Maniatis et al. in "Molecular Cloning—a laboratory manual", Cold Spring Harbor Laboratory 1982). Such substantially homologous nucleotide sequences may contain single or multiple nucleotide substitutions and/or deletions and/or additions thereto.

Most preferably, the isolated DNA molecule comprises a nucleotide sequence substantially corresponding to that shown in Table 1 from residue −942 to −1.

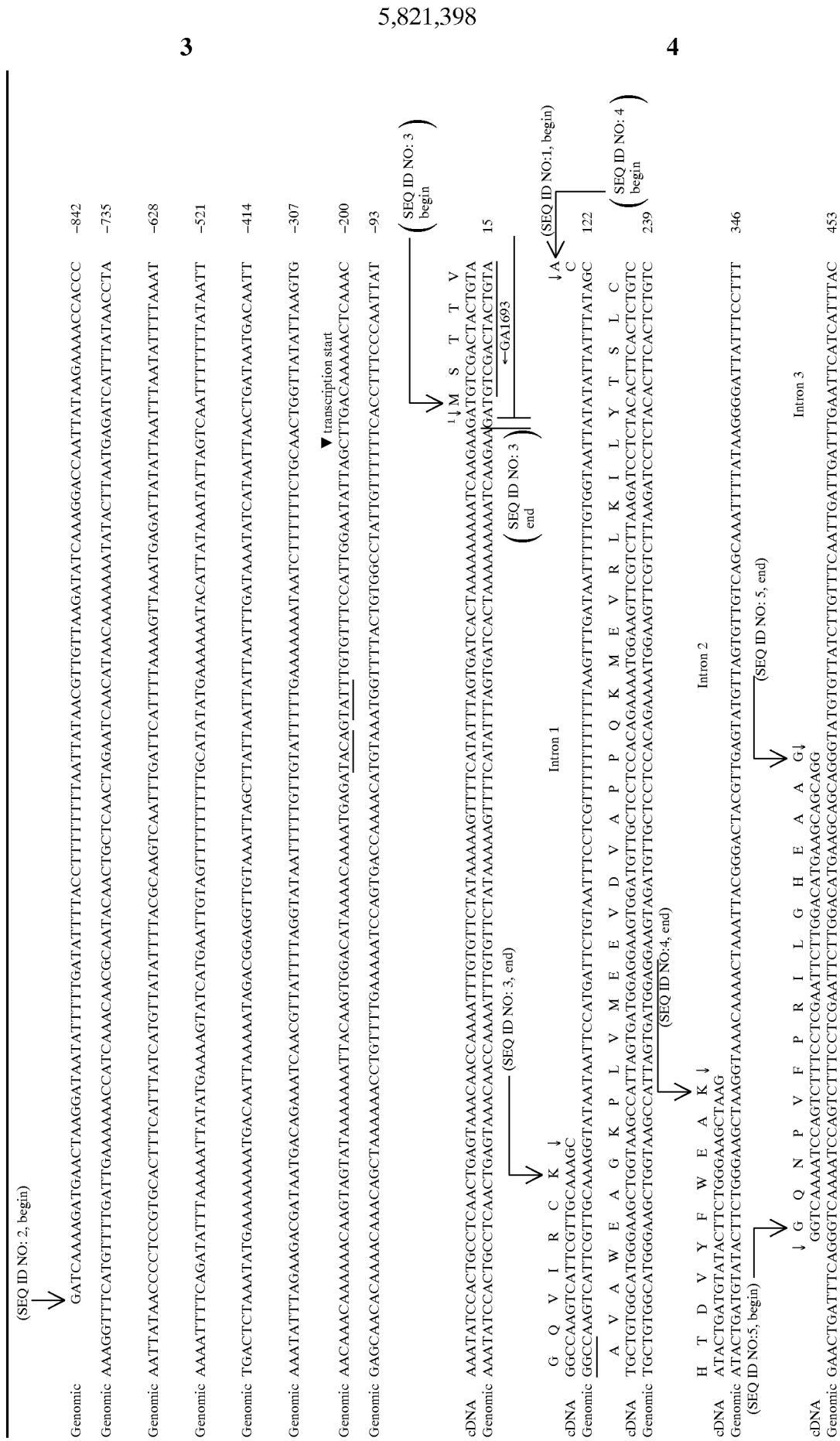

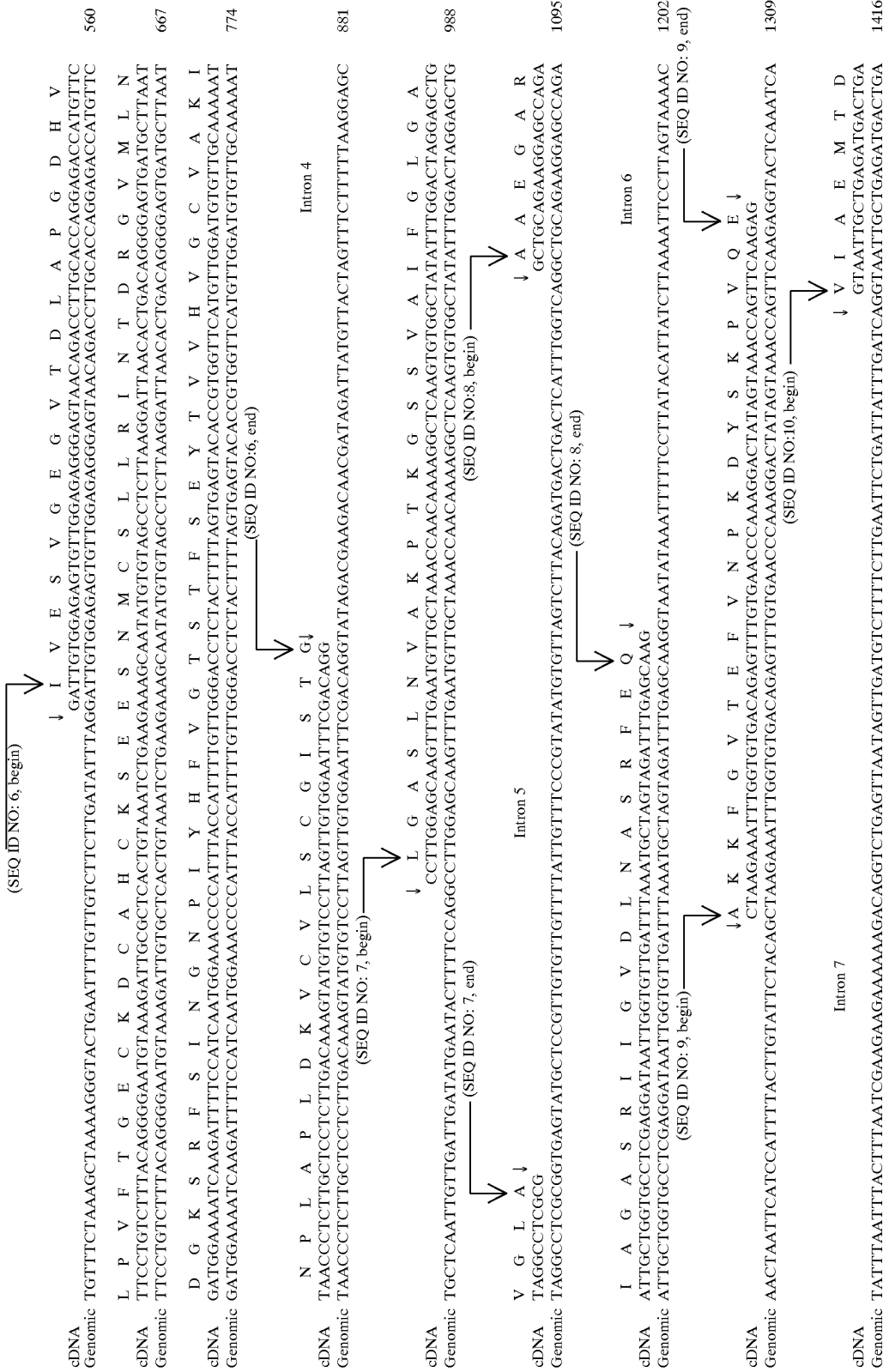

```
                    G  G  V  D  R  S  V  E  C  T  G  H  I  D  A  M  I  S  A  F  E  C  V  H  D
cDNA      TGGCGGAGTCGATAGGAGTGTGGAATGTACGGGTCACATTGATGCTATGATTTCAGCATTTGAATGTGTCCATGATG                                          1523
Genomic   TGGCGGAGTCGATAGGAGTGTGGAATGTACGGGTCACATTGATGCTATGATTTCAGCATTTGAATGTGTCCATGATG
                                                                          (DEQ ID NO:10, end)      Intron 8 →
                            ↓ G  W  G  V  A  V  L  V  G  V  P  H  K  E  A  V  F  K  T
cDNA                          GCTGGGGAGTGGCGGTTCTGTTGGTGTACCCCATAAAGAAGCTGTGTTCAAGACAC           1630
Genomic   AGCTGTATGTTTGCGTTCATCTTAACGAACATTGTTGTATTAACTTTAGGGCTGGGGAGTGGCGGTTCTGTTGGTGTACCCCATAAAGAAGCTGTGTTCAAGACAC
                              (SEQ ID NO:11, begin)

H  P  L  N  F  L  N  E  R  T  L  K  G  T  F  F  G  N  Y  K  P  R  S  D  I  P  C  V  V  E  K  Y  M  N  K  E
cDNA      ATCCCTCGAACTTTTTGAATGAACGGACTCTCAAAGGAACCTTCTTTGGAAATACAAACCTCGTTGTGGAAAAATACTACAAAACCTCGTTGTTGAGAAATACATGAACAAAGAA   1737
Genomic   ATCCCTCTGAACTTTTTGAATGAACGGACTCTCAAAGGAACCTTCTTTGGAAATACAAACCTCGTTGTTGAGAAATACATGAACAAAGAA L  E  L  E  K  F  I  T  H  T  L  P  F  A  E  I  N  K  A  F  D  L  M  L  K  G  E  G  L  R  C  I  I  T  M  A
cDNA      CTTGAATTGGAGAAATTCATCACTCATACACTTCCATTTGCTGAAATCAATAAGGCTTTCGATTTAATGCTGAAGGGAGAAGGCCTTCGTTGCATCATCACCATGGC             1844
Genomic   CTTGAATTGGAGAAATTCATCACTCATACACTTCCATTTGCTGAAATCAATAAGGCTTTCGATTTAATGCTGAAGGGAGAAGGCCTTCGTTGCATCATCACCATGGC
                                                                              (SEQ ID NO:11, end)
          ↓
          D  *
cDNA      GGACTAAACTTTCTGTCCTAGAAAAGGAGCTTCTACTGTTTGAGAAAAAAGACCAATAAATTGTCACTGTCTTATTTTCCCTTTCGTGTTTGGTTGAGTTGTAACAT           1951
Genomic   GGACTAAACTTTCTGTCCTAGAAAAGGAGCTTCTACTGTTTGAGAAAAAAGACCAATAAATTGTCACTGTCTTATTTTCCCTTTCGTGTTTGGTTGAGTTGTAACAT cDNA      TCCATCCATGTCTCTCTTTTGTCTTTTGCTTTGTGCTTTGTGCTTTAGATGTGTGCCATATCTCTTTTGCAATTCTCTCTGTTTATCTCAAGTATAT                     2058
Genomic   TCCATCCATGTCTCTCTTTTGTCTTTTGCTTTGTGCTTTGTGCTTTAGATGTGTGCCATATCTCTTTTGCCATATCTCTTTTGTAAAAAATGCAAATTCTCTCTGTTTATCTCAAGTATAT cDNA      TTACAGAATTTCAGTGATTTGATAAATCTAAACTTTATCATAATATATCCAAACAGAATTTCAATTGAAAAAAA                                             2175
Genomic   TTACAGAATTTCAGTGATTTGATAAATCTAAACTTTATCATAATATATCATAATATATCCAAACAGAATTTCAATTGAAAAATGATGAAGGCCCTTACCGTCATTGTCC
                                                                                                (SEQ ID NO:1, end)
```

In order to isolate the tomato ADH2 promoter, it was necessary to first isolate the tomato ADH2 encoding sequence. The present inventors have thus isolated a cDNA (see Table 1) which was used to prepare hybridisation probes for isolation of a genomic fragment encoding ADH2 and containing the ADH2 promoter sequence.

In a third aspect, the present invention provides an isolated DNA molecule comprising a nucleotide sequence encoding a plant promoter obtained from a genomic fragment isolated using a labelled nucleic acid probe comprising a nucleotide sequence substantially corresponding to the cDNA sequence or a portion thereof shown in Table 1.

The probe may be DNA or RNA transcripts.

DNA molecules according to any of the preceding aspects may further comprise nucleotide sequences encoding peptides or polypeptides expressibly linked to the promoter sequence. The peptide or polypeptide may be involved in fruit softening, flavour, colour or aroma, for example polygalacturonase or its subunits, pectin methyl esterase, xyloglucanase or other beta-1,4-glucanases, glycosidases, beta-galactosidase, alcohol dehydrogenase or lipoxygenase. Further, ripe fruit are more susceptible than unripe fruit to fungal invasion. Thus the peptide or polypeptide encoding sequence may encode fungal resistance agents (e.g. chitinase, beta-1,3-glucanase) or other plant pathogen resistance agents.

The peptide or polypeptide encoding sequence or a portion thereof (e.g. a 20–50 nucleotide portion), may be linked in the opposite orientation for expression in a 3' to 5' direction such that antisense RNA is produced.

Ribozymes for cleaving mRNA's encoding the peptide or polypeptide may be produced in a similar manner. In this case, the oppositely orientated nucleotide sequences provide the ribozymes with specificity and a further nucleotide sequence encodes a catalytic domain for cleavage of mRNA. Suitable catalytic domains include hammerheads, hairpins, delta-virus elements, ribosome RNA introns and their derivatives. Further information regarding the design of ribozymes can be found in Haseloff, J. & Gerlach, W. L. (1988) Nature Vol. 334:585, and Kruger, K. et al. (1982) Cell Vol. 31, 147; International Patent Application No. WO 88/04300, U.S. Pat. No. 4,987,071 and U.S. Pat. No. 5,254, 678. The disclosure of each of these references is incorporated herein by reference.

Further, DNA molecules according to the invention may include enhancer elements (e.g. from the octapine synthase gene of *Agrobacteriwm tumefaciens*—Ellis, J. G. et al., 1987 EMBO J. 6:11–16), or multiple copies of an anaerobic response element (ARE) (Olive, M. R. et al., 1990 Plant Mol. Biol. 15: 593–604), or intron sequences.

The tomato ADH2 enzyme is believed to be involved in fruit ripening by metabolising hexanols/als and methoxybutanols/als, which are important fruit flavour volatiles. By modifying the activities and/or abundance, in ripening fruit, of the enzymes involved in production of flavour volatiles, it is possible to increase their production of flavour volatiles independently of the rate of fruit softening and thereby enhance development of flavour in the fruit. Thus, transgenic plants with modified ADH2 levels may have direct commercial value and provide valuable stocks for breeding programs.

Thus, in a fourth aspect, the present invention provides an isolated DNA molecule comprising a nucleotide sequence encoding tomato ADH2 or a fruit ripening and/or aroma/flavour-affecting portion thereof.

Preferably, the isolated DNA molecule comprises a nucleotide sequence substantially corresponding to the cDNA sequence shown in Table 1 or the genomic sequence from residue 1–2175 shown in Table 1.

The term "substantially corresponding" as used herein in relation to the nucleotide sequence encoding tomato ADH2 or a fruit ripening and/or aroma/flavour-affecting portion thereof, is intended to encompass minor variations in the DNA sequence which due to degeneracy in the DNA code do not result in a significant change in the encoded protein. Further this term is intended to encompass other minor variations in the sequence which may be required to enhance expression in a particular system but in which the variations do not result in a decrease in biological activity of the encoded protein.

Preferably, the isolated DNA molecule according to the fourth aspect encodes an ADH2 or a fruit ripening and/or aroma/flavour-affecting portion thereof that is normally expressed during natural fruit ripening and further comprise a suitable constitutive promoter (e.g. CaMV 35 S promoter) or an inducible promoter, such as the promoter according to any one of the first to third aspects of the invention, or endopolygalacturonase, 1-aminocyclopropane-1-carboxylic acid oxidase or E8 promoters, expressibly linked to the ADH2 encoding sequence.

The ADH2 encoding sequence or a portion thereof (e.g. a 20–50 nucleotide portion) may be linked to the promoter in the opposite orientation for expression in a 3' to 5' direction such that antisense RNA is produced. By further including a nucleotide sequence encoding a catalytic domain, ribozymes targetted against ADH2 mRNA's may also be produced. Further, DNA molecules according to the fourth aspect of the invention may include enhancer elements or multiple copies of the anaerobic response element.

In a further aspect, the present invention provides a plant transformed with at least one DNA molecule according to any one of the first, second, third or fourth aspects.

In some applications, it may be preferred to transform the plant with multiple copies of a DNA molecule according to any one of the first, second, third or fourth aspects.

Preferably the DNA molecule(s) is stably inserted into the plant genome and will be transferred, via the seed or by clonal propagation, to subsequent generations.

Transformation may be via, for example, *Agrobacterium tumefaciens*-mediatec transfer or the DNA particle gun method.

The invention thus permits suitable "slow ripening" "slow softening" soft fruit cultivars to be transformed with hybrid DNA molecules to enable the production of wall loosening, colour-affecting and/or aroma/flavour enhancing enzymes. Where an inducible promoter is used, production of the enzyme(s) can be controllably regulated by, for example, selected temperature or gaseous treatments applied at a late stage in the fruit distribution and marketing chain.

In a specific case, benefits can be envisaged in modifying a slow-ripening tomato cultivar by incorporation of a hybrid DNA molecule comprising the ADH2 promoter from tomato, suitable enhancers, and the tomato polygalacturonase gene or ADH2 gene. During the early stages of distribution after harvesting advantage could be taken of the cultivar's inherent resistance to physical damage, but the promoter could be activated, at a point close to sale, to bring out a flavour akin to that of a fast ripening cultivar.

Northern analysis of ripening fruit of two tomato cultivars has shown that the mRNA for ADH2 is present in low abundance in mature green fruit and increases in abundance through ripening and, particularly, late in ripening. In fruit pericarp tissue exposed to atmospheres with 3% (v/v) oxygen, the ADH2 mRNA level increases to a maximum within 8–16 hours, and returns to the basal level within 16 hours of return to air. The mRNA level was sensitive to the oxygen level in the atmosphere, increasing 20 fold in 12% (v/v) oxygen and 100 fold in 3% oxygen. These oxygen levels may reflect appropriate levels for the induction of some inducible promoters according to the invention in commercial amounts of fruit harvested from tranegenic plants. Alternative methods for induction may include UV light, low temperatures (e.g. 0°10° C.) and exposure to some organic acids including gaseous $CO_2$.

Although, the inducible promoters envisaged by the invention are particularly described in relation to their expression in soft fruit, it should be appreciated that the promoters may be activated by the environmental agents and conditions in other tissues.

The invention will now be further described by way of the following, non-limiting examples and with reference to the accompanying figure.

EXAMPLE 1

Figure 1:
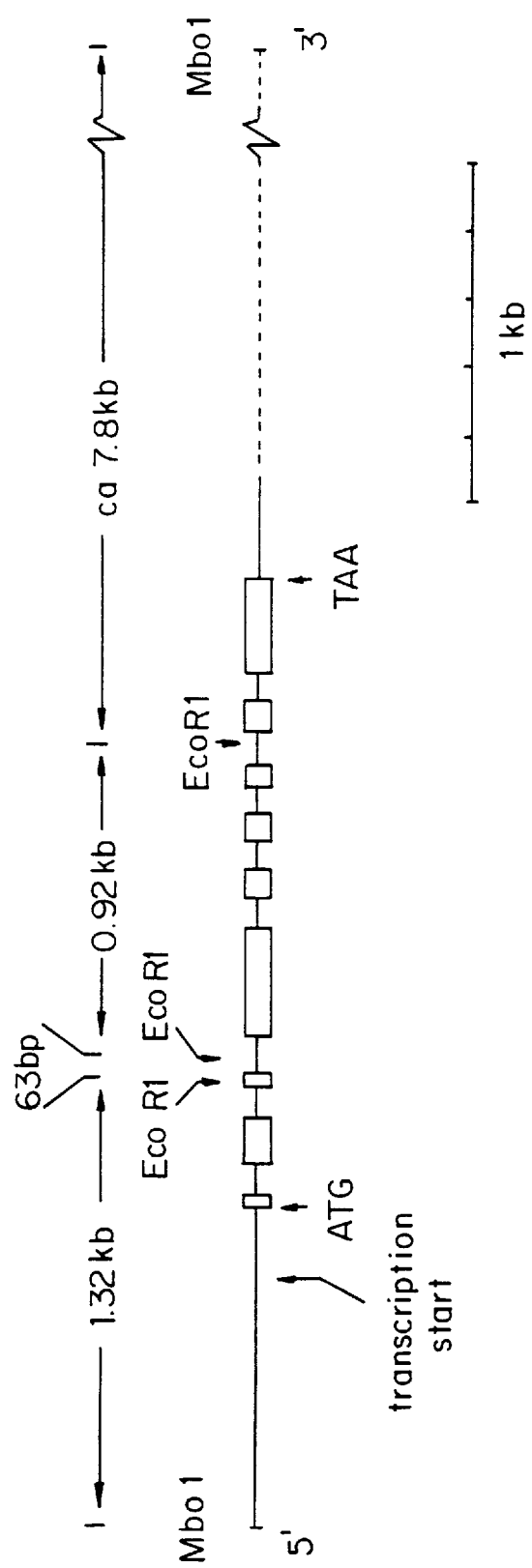
FIG. 1 is a diagram of the genomic clone lambda 2A3 indicating the location of axons 1 to 9 of the ADH2 gene, the relative positions of the EcoR1 fragments and the 5' region comprising the promoter The region shown dashed has not been sequenced.

Isolation of a cDNA Encoding Tomato ADH2

Poly A$^+$RNA was isolated from pericarp tissue of tomato (cv. de Ruiter 83G38) fruit, 9 days after the first appearance of colour (Breaker+9). A cDNA library was constructed from the poly A$_+$RNA and was cloned into lambda Gem 11 using the protocol of Promega Ltd. The library was screened by hybridisation with a $^{32}$p-labelled fragment of tomato genomic DNA with sequence homology to ADH genes of pea (Llewellyn et al. J. Mol.Bio. 195:115–123, 1987) potato (Matton et al., Plant Mol.Biol. 14:775–783, 1990) and maize (Dennis et al. Nucleic Acids Res. 13:727–743, 1985). Four positive colonies were isolated, phage DNA was purified and CDNA inserts were transferred from the phage vector to a plasmid vector pGem 11 (Promega) for sequencing. Sequencing was carried out by the dideoxy-method of Sanger et al. PNAS, USA 74:5463–5467 (1977) on double stranded DNA using pUC universal and reverse primers and oligonucleotide primers to extend known sequence. The four cDNAs had identical 5' sequences and identical open reading frames encoding a protein of 364 amino acids.

The cDNA hybridised strongly to a 1.6 kb RNA species in RNA from ripe but not from unripe tomato fruit.

Similarly, the cDNA hybridised to RNA from tomato seedling roots kept anaerobic overnight, but not to RNA from aerobic roots. In contrast, a Bgl11 fragment of tomato genomic cDNA, which contains regions encoding the tomato ADH1 isozyme and hybridises strongly to ADH1 MRNA but weakly to ADH2 mRNA (Wisman et al. Mol. & Gen. Genet. 226:120–128, 1991), did not hybridise to RNA from either ripe fruit or anaerobic root tissue. Thus it was concluded that the cDNAs isolated from the ripening fruit library, encode a tomato ADH2 enzyme.

The nucleotide sequence for the cDNA encoding the ADH2 mRNA is provided at Table 1.

The 5' 843 nucleotides of the CDNA including sequence encoding 250 amino acids of the ripening associated ADH2 enzyme provides a particularly useful probe by virtue of its location adjacent to the promoter in the genomic sequence.

EXAMPLE 2

Isolation of Tomato ADH2 Promoter

Isolation of Tomato Leaf DNA.

Young leaves of tomato plants (cv. de Ruiter 83G38) were harvested and snap-frozen in liquid nitrogen. The leaves were ground to a fine powder under liquid nitrogen and DNA was isolated by the method of Thomas et al. Theor. Appl. Genetics 86:173–180 (1993).

Construction of Genomic Library.

Aliquots of high molecular weight tomato genomic DNA were digested with varying amounts of Mbol restriction endonuclease for 1 hour at 37° C. and digestion was stopped by heating the samples at 75° C. for 10 minutes.

The samples were fractionated on a 0.5% agarose gel and the mean size and spread of the digested DNA was determined. 20µg of genomic DNA as digested with Mbol enzyme, under conditions designed to give a fragment size range of between 10 kb and 20 kb, and the reaction was stopped as before. The digested fragments were partially end-filled with dATP and dGTP and were ligated into Lambda GEM-11 Xho1 Half-site arms (Promega Corp.), according to the Promega protocols. Three ligations were carried out with arms: fragment ratios of: 0.5 µg:0.25 µg; 0.5 µg:0.5 µg; 0.5µg:0.75µg.

The ligated DNA samples were packaged according to Hohn, Methods in Enzymology 68:299–309 (1979) and titred, giving average titres of 1.8×10$^5$ pfu/µg arms. The three libraries were pooled.

Library Screening.

*E. coli*, strain KW251 cells, were infected with 2×10$^5$ phage, were spread on six, 10 cm×10 cm Luria agar plates (33,000 pfuJplate) and were incubated at 37° C. for 6 hours until small phage plaques had developed. Lifts were taken off the plates onto Biotrace NT nitrocellulose membranes (Gelman Sciences), and the membranes were prehybridised, hybridised and washed according to the Gelman protocols. Dried membranes were exposed to X-ray film (Fuji, RX) with an intensifying screen (Du Pont—Cronex, Lightning-Plus) at –70° C. Hybridisation probes were labelled with $^{32}$p dATP by oligopriming (Feinberg and Voglestein, Anal. Biochem 132:6–13, 1983).

Subeloning and Sequencing.

The genomic DNA insert of lambda clone 2A3 was digested with EcoR1 restriction enzyme and the resulting fragments subcloned by ligation into the plasmid vector pUC18 (Yanisch-Peron et al., Gene 33:103–119, 1985) by standard methods.

Double stranded sequencing was carried out by the enzymatic chain-termination method of Sanger et al.

Proc. Natl. Acad. Sci. USA 74: 5463–5467 (1977), using universal and reverse M13 primers based on determined sequence.

PCR amplification of the 5' region of the ADH2 gene was carried out on a tomato genomic DNA template using oligonucleotide primers to regions of the AHD2 cDNA as follows:

5' Primer #1078 5' CCACTGCCTCAACTGAG 3' (SEQ ID NO:12)

3' Primer #1057 3' CGACCATTCGGTAATCA 5' (SEQ ID NO:13)

PCR reactions were carried out in 50 μl reactions containing 16.6 mM (NH)$_4$SO4, 67 mM Tris-HCl pH 8.8, 6.7 mM EDTA, 2 mM MgCl$_2$, 0.15% Triton X-100, 200 μM dNTPs and 200 μg/μl gelatin, with primers added at 22 pmol/μl, 100 ng tomato genomic DNA and 2.5 units of Taq polymerase. Reactions were carried out as follows:

| 1st cycle: | 94° C. 5 mins. |
|---|---|
| | 45° C. 1 min. |
| | 72° C. 1 min. |
| Followed by 38 cycles as follows: | |
| | 94° C. 1 min. |
| | 45° C. 1 min. |
| | 72° C. 1.5 mins. |

The PCR product was ligated into pBluescript KS$^+$vector (Stratagene) linearised at the EcoRV site and T-tailed according to the procedure of Marchuk et al. Nucleic Acids Research 19.1154 (1990).

Results

Duplicate lifts were taken of six plates containing a total of 2×10$^5$ pfu of a phage library of tomato genomic DNA. The lifts were screened by hydridisation with two probes. The first probe, pADHCR1 was designed to be specific to the 5' end of the tomato AHD2 gene which is expressed in ripening fruit. PADHCR1 was generated by PCR amplification of the genomic sequence bounded by primers #1078 and #1057 defined by the sequence of the ADH2 cDNA and spans exon 1, intron 1 and 34 nucleotides of exon 2 of the ADH2 gene. The second probe, pADH2-3' constitutes the entire ADH2 cDNA 3' of the EcoR1 site at nucleotide 290 on the CDNA (nucleotide 382 on the genomic DNA—Table 1).

Screening with the 5' specific probe, pADHCR1, gave 28 positives. Screening with the 3 ' specific probe, pADH2-3' gave 20 positives. Only one lambda phage plaque, 2A3, hybridised with both probes, and this plague was isolated and purified for further characterisation.

EcoR1 digestion of DNA from the lambda genomic clone, 2A3, generated a number of fragments including the left and right arms of the lambda vector and three fragments of insert DNA with sizes of 7.8 kb, 1.4 kb and 1.2 kb. Subsequent subcloning revealed a further insert fragment of 63 bp in size. The EcoR1 fragments were subcloned into pUC18 and were sequenced, allowing alignment of the fragments to be determined (FIG. 1). The 1.4 kb subclone, pADH2-1.4 was found to contain the 5' end of the ADH2 gene, from the EcoR1 site at nucleotide 290 in the cDNA and including introns 1 and 2. The clone includes the transcription start site and extends a further 800 bp upstream encompassing the gene promoter.

The sequence of the clone 2A3 including the ADH2 promoter and the protein-encoding region (including introns) is provided at Table 1. The ADH2 gene has an overal length of 2334 bp from transcription site to poly A addition site.

Two regions, with a core sequence of 5'-AAACAA-3', showing homology to anaerobic response elements found in other dicots, are arranged in tandem upstream and close to the putative transcription start site, between positions −313 and −240. One inducible promoter portion of the ADH2 promoter may therefore comprise these regions, e.g. residues −350 to −1 of Table 1.

EXAMPLE 3

Production of Transformed Tomato Plants Expressing ADH2

The CDNA for tomato ADH2 described in Example 1 may be coupled in a normal orientation to the constitutive plant promoter CaMV 35S promoter. The chimeric gene may then be introduced into a suitable expression vector, which is subsequently used to transform tomato cells by any of the methods commonly known in the art.

Transformed plants may be analysed for the presence of the introduced ADH2 construct and for its expression. Correct synthesis of ADH2 enzyme will be checked by expression in bacterial cells transformed with the construct.

Positive plants (T0) will be selfed and homozygous transformants (T1) will be selected. ADH2 mRNA levels and ADH2 enzyme activity will be analysed in fruit from T1 plants.

Finally, volatile components of fruit will be analysed and fruits will be subjected to sensory evaluation.

By a similar method, transformed tomato plants may be produced which show a decreased expression of ADH2 in ripening fruit.

In this case however, the ADH2 cDNA shall be linked to the promoter in reverse orientation such that antisense RNA shall be produced.

EXAMPLE 4

Production of Transformed Plants Expressing Polypeptide-Encoding DNA Sequences Using the ADH2 Promoter The tomato ADH2 promoter described in Example 2 may be coupled to a nucleotide sequence encoding a polypeptide such as the tomato polygalacturonase enzyme. The chimeric gene may then be introduced into a suitable expression vector, which can be subsequently used to transform tomato cells.

Expression of the introduced gene in transformed plants may be allowed to occur naturally during fruit ripening or may be induced by exposure of plant tissue to, for example, reduced oxygen atmospheres.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. An isolated DNA molecule comprising the nucleotide sequence of Table 1, residue −942 to −1 (SEQ ID NO:2), encoding a soft fruit promoter wherein said promoter is characterized in that it can be activated by environmental agents selected from the group consisting of low temperature, UV light, or exposure to particular levels of oxygen, carbon dioxide, carbon monoxide or organic acids and wherein said promoter or functional portion thereof is activated, or primarily activated, during a late state of normal soft fruit ripening.

2. An isolated DNA molecule according to claim 1 wherein the activating environmental agent is low temperature.

3. An isolated DNA molecule according to claim 1 wherein the activating environmental agent is exposure to UV light.

4. An isolated DNA molecule according to claim 1, wherein the activating environmental agent is exposure to particular levels of oxygen, carbon dioxide, or carbon monoxide.

5. An isolated DNA molecule according to claim 1, wherein the soft fruit promoter or functional portion thereof is from grapes, strawberries, peaches, plums or tomatoes.

6. An isolated DNA molecule comprising a nucleotide sequence encoding the tomato ADH2 promoter according to claim 1.

7. An isolated DNA molecule comprising a nucleotide sequence which corresponds to the cDNA sequence shown in Table 1 (SEQ ID NO:2), said nucleotide sequence encoding a plant promoter obtained from a genomic fragment isolated using a labelled nucleic acid probe comprising a nucleotide sequence the cDNA sequence or a portion thereof shown in Table 1.

8. An isolated DNA molecule according to claim 1, further comprising a nucleotide sequence encoding a peptide or polypeptide operably linked to the promoter sequence.

9. An isolated DNA molecule according to claim 8, wherein the peptide or polypeptide is involved in fruit softening, flavour, colour or aroma.

10. An isolated DNA molecule according to claim 9, wherein the peptide or polypeptide is selected from the group consisting of polygalacturonase or its sub-units, pectin methyl esterase, xyloglucanase or other β-glucanases, glycosidases, β-galactosidase, alcohol dehydrogenase and lipoxygenase.

11. An isolated DNA molecule according to claim 8, wherein the peptide or polypeptide is a fungal resistance agent or other plant pathogen resistance agent.

12. An isolated DNA molecule according to claim 11, wherein the peptide or polypeptide is chitinase or β-1,3-glucanase.

13. An isolated DNA molecule comprising at least a nucleotide portion of a nucleotide sequence encoding a peptide or polypeptide, wherein the at least 20 nucleotide portion is linked to the la promoter sequence as provided by a DNA molecule according to claim 1, in the opposite orientation for expression in a 3' to 5' direction such that antisense RNA is produced.

14. An isolated DNA molecule according to claim 13, further comprising a nucleotide sequence encoding a catalytic domain such that expression results in the production of ribozymes for cleaving mRNA's encoding the peptide or polypeptide.

15. An isolated DNA molecule claim 14, comprising a nucleotide sequence which corresponds to the cDNA sequence shown in Table 1 (SEQ ID NO:1 nucleotides 1–37; 122–207; 350–396; 495–821; 908–989; 1068–1143, 1226–1287; 1387–1450; and 1564–1840), said nucleotide sequence encoding tomato ADH2.

16. An isolated DNA molecule comprising a nucleotide sequence which corresponds to the genomic sequence from residue 1–2147 shown in Table 1 (SEQ ID NO;1), said nucleotide sequence encoding tomato ADH2.

17. An isolated DNA molecule according to claim 15, further comprising an operably linked constitutive promoter or inducible promoter.

18. An isolated DNA molecule according to claim 17, wherein the operably linked promoter sequence is encoded by an isolated DNA molecule according to or is selected from the group consisting of the CaMV 35S promoter, the endopolygalacturonase promoter, 1-aminocyclopropane-1-carboxylic acid oxidase promoter or E8 promoter.

19. An isolated DNA molecule comprising of at least a 20 nucleotide portion of the ADH2-encoding sequence as provided by a DNA molecule according to claim 15, wherein the at least 20 nucleotide portion is linked to a constitutive or inducible promoter sequence in the opposite orientation for expression in a 3' to 5' direction such that antisense RNA is produced.

20. An isolated DNA molecule according to claim 19, further comprising a nucleotide sequence encoding a catalytic domain such that expression results in the production of ribozymes for cleaving mRNA's encoding ADH2.

21. A plant transformed with at least one DNA molecule according to claim 15.

22. A plant according to claim 21, wherein the plant has been transformed with multiple copies of a DNA molecule according to claim 17.

23. The isolated DNA molecule according to claim 1, wherein said late stage of ripening is at least about 9 days from breaker.

* * * * *

UNITED STATES PATENT AND TRADEMARK OFFICE
CERTIFICATE OF CORRECTION

PATENT NO. : 5,821,398
DATED : October 13, 1998
INVENTOR(S) : James Speirs, et. al.

It is certified that error appears in the above-indentified patent and that said Letters Patent is hereby corrected as shown below:

Title page, item [75], Inventors: should read as followings:

James Speirs, Adelaide; Colin John Brady, Shoal Bay; Elizabeth Lee, Marsfield; Richard Hinde, Thornleigh; Terrence James Longhurst, Mt. Colah, all of Australia--.

Page 1, second column, line 35, "cds" should read cDNAs--; and
    Line 41, "Developmental Research" should read –Developmental Regulation.--

Page 2, first column, line 15, "Expression suring" should read –Expression during--; and
    Second column, delete lines 24-31.

Column 10, line 47, "tumefaciens-mediatec should read –tumefaciens-mediated--.

Column 11, line 11, "from tranegenic plants" should read –from transgenic plants--;
    Line 13, "(e.g. 0°10°C.)" should read –(e.g. 0°-10°C.)--;
    Line 26, "axons" should read –exons--;
    Line 38, "$^{32}$p-labelled" should read –$^{32}$P-labelled--;
    Line 44, "CDNA" should read –cDNA--;
    Line 49, delete the paragraph indentation; and
    Line 61, "MRNA" should read nRNA--.

Column 12, line 21, delete the paragraph indentation;
    Line 23, "DNA as digested" should read –DNA was digested--;
    Line 50, "Subeloning" should read –Subcloning--; and
    Line 56, delete the paragraph indentation.

Column 13, line 3, "50 µlreactions" should read 50 µl reactions--; and
    Line 37, "plague" should read –plaque--.

Column 14, line 11, "CDNA" should read –cDNA--.

Column 25, line 38, "cDNA" should read –genomic--; and
    Line 43, after "sequence" insert –which corresponds to--.

UNITED STATES PATENT AND TRADEMARK OFFICE
CERTIFICATE OF CORRECTION

PATENT NO. : 5,821,398
DATED : October 13, 1998
INVENTOR(S) : James Speirs, et. al.

It is certified that error appears in the above-indentified patent and that said Letters Patent is hereby corrected as shown below:

Column 26, line 11, "at least a" should read –at least a 20--;
Line 14, "the la promoter" should read –a promoter--;
Line 23, "molecule claim 14" should read –molecule according to claim 14--;
Line 38, "according to or is selected" should read –according to claim 15 or is selected--; and
Line 57, "according to claim 17" should read –according to claim 15--.

Signed and Sealed this

Sixteenth Day of November, 1999

Attest:

Attesting Officer

Q. TODD DICKINSON

Acting Commissioner of Patents and Trademarks